United States Patent
Davis

(10) Patent No.: US 10,502,727 B2
(45) Date of Patent: Dec. 10, 2019

(54) ACOUSTIC MONITORING OF BLOCK CAVING

(71) Applicant: CiDRA Corporate Services Inc., Wallingford, CT (US)

(72) Inventor: Michael A. Davis, Glastonbury, CT (US)

(73) Assignee: CiDRA Corporate Services LLP, Wallingford, CT (US)

( * ) Notice: Subject to any disclaimer, the term of this patent is extended or adjusted under 35 U.S.C. 154(b) by 1452 days.

(21) Appl. No.: 14/380,590

(22) PCT Filed: Feb. 28, 2013

(86) PCT No.: PCT/US2013/028232
§ 371 (c)(1),
(2) Date: Aug. 22, 2014

(87) PCT Pub. No.: WO2013/130745
PCT Pub. Date: Sep. 6, 2013

(65) Prior Publication Data
US 2015/0019133 A1    Jan. 15, 2015

Related U.S. Application Data

(60) Provisional application No. 61/604,062, filed on Feb. 28, 2012.

(51) Int. Cl.
*G01N 33/24* (2006.01)
*G01S 3/808* (2006.01)
(Continued)

(52) U.S. Cl.
CPC ............. *G01N 33/24* (2013.01); *E21C 41/22* (2013.01); *G01S 3/808* (2013.01); *G01S 15/89* (2013.01); *G01V 1/00* (2013.01); *G01S 5/20* (2013.01)

(58) Field of Classification Search
CPC .... G01S 5/10; G01V 1/00; G01V 1/50; E21B 49/00; E21B 47/0002; E21B 47/02; F17D 5/02
(Continued)

(56) References Cited

U.S. PATENT DOCUMENTS 4,779,201 A * 10/1988 Iizuka ................. E21B 47/0002
                                                          324/338
5,024,090 A *  6/1991 Pettigrew ................. G01V 1/00
                                                          73/572
(Continued)

OTHER PUBLICATIONS

John Sogade 'Electromagnetic Cave-to-surface Mapping System' (Year: 2004).*

(Continued)

*Primary Examiner* — Regis J Betsch
*Assistant Examiner* — Kaleria Knox
(74) *Attorney, Agent, or Firm* — Ware, Fressola, Maguire & Barber LLP

(57) ABSTRACT

Apparatus is provided featuring a signal processing module configured to receive signaling containing information about detected acoustic emissions related to ore being mined from a block cave in a block caving process, including falling ore that creates unique acoustic signatures; and determine information about the ore being mined from the block cave in the block caving process, based at least partly on the signaling received. The signal processing module may receive the signaling from an array of acoustic sensors placed around the block cave, including where the array of acoustic sensors surrounds the block cave in both vertical and horizontal directions. The signal processing module may provide corresponding signaling containing corresponding information about the ore being mined from the block cave in the block caving process, including where the corresponding informa- (Continued)

tion includes information about a distribution and size of the ore being mined from the block cave in the block caving process.

44 Claims, 2 Drawing Sheets

(51) Int. Cl.
    *G01S 15/89*     (2006.01)
    *E21C 41/22*     (2006.01)
    *G01V 1/00*     (2006.01)
    *G01S 5/20*     (2006.01)

(58) Field of Classification Search
    USPC .......................................... 73/572; 324/334
    See application file for complete search history.

(56) References Cited

U.S. PATENT DOCUMENTS

| | | |
|---|---|---|
| 5,051,965 A | 9/1991 | Poorman |
| 5,206,840 A | 4/1993 | Cobbs et al. |
| 7,471,592 B2 | 12/2008 | Turgut |
| 7,882,750 B2 | 2/2011 | Davis et al. |
| 8,336,393 B2 | 12/2012 | Davis et al. |
| 2003/0173819 A1 | 9/2003 | Hames et al. |
| 2006/0225507 A1* | 10/2006 | Paulson ............... F17D 5/02 73/592 |
| 2008/0306692 A1* | 12/2008 | Singer ............... G01V 1/50 702/11 |
| 2010/0024551 A1 | 2/2010 | Maguire et al. |
| 2010/0095757 A1* | 4/2010 | Hansen ............. G01N 29/043 73/152.16 |
| 2011/0006774 A1* | 1/2011 | Baiden ............. G01S 5/10 324/334 |
| 2011/0208447 A1 | 8/2011 | Davis et al. |

OTHER PUBLICATIONS

A. Nehorai et al., entitled, "Acoustic Vector-sensor array processing," IEEE Transactions on Signal Processing, vol. 42, No. 9, Sep. 1994, pp. 2481-2491.

* cited by examiner

Apparatus 10

Signal processor 10a configured to receive signaling containing information about detected acoustic emissions related to ore being mined from a block cave in a block caving process, including falling ore that creates unique acoustic signatures; and determine information about the ore being mined from the block cave in the block caving process, based at least partly on the signaling received.

Other modules 10b for implementing the signal processing functionality, including a memory module, data and control busing architecture and input/output modules.

Figure 1

ACOUSTIC MONITORING OF BLOCK CAVING

CROSS-REFERENCE TO RELATED APPLICATIONS

This application corresponds to international patent application serial no. PCT/US2013/028232, filed 28 Feb. 2013, which claims benefit to provisional patent application Ser. No. 61/604,062 (CCS-0079), filed 28 Feb. 2012, which is incorporated by reference in their entirety.

BACKGROUND OF THE INVENTION

1. Field of Invention

The present invention relates to techniques for mining particles of interest; and more particular to techniques for mining particles of interest using acoustic monitoring of block caving.

2. Description of Related Art

Block caving is a newer technique used to mine massive steeply dipping ore bodies (typically low grade) with high friability (i.e., excessive breakableness). An undercut with haulage access is driven under the ore body, with "drawbells" excavated over the undercut. The drawbells serve as a place for caving rock to fall into. The ore body is drilled and blasted above the undercut, and the ore is removed via the haulage access. Due to the friability of the ore body, the ore above the first blast caves falls into the drawbells. As ore is removed from the drawbells, the ore body caves in providing a steady stream of ore.

Block caving in mining has several advantages over traditional pit mining including the potential for reduced energy usage.

However, one problem with the known block caving techniques is related to difficulties in determining the progression of the ore material as it passes down through the caving area to the bottom.

Another problem with the known block caving techniques is related to difficulties in determining if there are voids or stuck areas of the block as it progresses.

In effect, in order to optimize the block caving process mine engineers would like to be able to map out the progression of the ore material as it passes down through the caving area to the bottom. Ideally, a detailed picture of the ore progression would let the mine engineers know if there are voids or stuck areas of the block as it progresses. Other important details would also be of interest such as a picture of the rock size as it is crushed by the falling ore body.

SUMMARY OF THE INVENTION

According to some embodiments, the present invention may take the form of apparatus featuring a signal processor or processing module configured at least to:
  receive signaling containing information about detected acoustic emissions related to ore being mined from a block cave in a block caving process, including falling ore that creates unique acoustic signatures; and
  determine information about the ore being mined from the block cave in the block caving process, based at least partly on the signaling received.

According to some embodiment of the present invention, the signal processor or processing module may be configured to provide corresponding signaling containing corresponding information about the ore being mined from the block cave in the block caving process, including where the corresponding information includes information about a distribution and size of the ore being mined from the block cave in the block caving process.

The present invention may include one or more of the following features:

The signal processor or processing module may be configured to receive the signaling from an array of acoustic sensors placed around the block cave, including where the array of acoustic sensors surrounds the block cave in both vertical and horizontal directions.

The signal processor or processing module may be configured to receive the signaling from an array of sensors detected at different times depending on the distance of individual acoustic generators from the array of sensors, including where the individual acoustic generators are falling and crushing rock.

The signal processor or processing module may be configured to use one or more array processing algorithms to localize the unique acoustic signatures providing information about locations of the detected acoustic emissions, based at least partly on the signaling received.

The signal processor or processing module may be configured to construct a 3-dimensional map that details origins of acoustic sources and a progression of the ore moving down the block cave, based at least partly on the signaling received.

The signal processor or processing module may be configured to determine information about stuck rock formations that do not behave as an acoustic source, permitting detection of regions where the block caving process is not progressing uniformly, based at least partly on the signaling received.

The signal processor or processing module may be configured to determine a degree of crushing as the ore moves in the block cave, based at least partly on the signaling received.

The signal processor or processing module may be configured to correlate frequency components of acoustically generated signals to the size of rocks falling and striking each other, including where smaller sized rocks create higher frequency components in acoustic signatures and larger sized rocks create lower frequency components in the acoustic signatures, allowing detection of the frequency components through Fourier analysis of the signaling received.

The signal processor or processing module also may be configured to determine a substantially full 3-dimensional image or picture of the ore that contains information on the progression of falling rock, along with rock size in each area of the block cave, based at least partly on the signaling received.

The signaling contains information about acoustic waves produced by an active acoustic source that impinge on a block of ore and reflect back acoustic energy sensed by an array of acoustic sensors. Moreover, the signal processor or processing module may also be configured to determine the location of rocks along with a degree of fragmentation of the rocks based at least partly on the signaling received. Moreover still, the apparatus may form part of an acoustic tomography system configured with pairs of acoustic transmitters/receivers that can alternately source and receive acoustic signals.

The signal processor or processing module may be configured to process received acoustic signals and determine the distribution and size of the rocks within the block cave.

The signal processor or processing module may be configured to determine a distribution and size of rocks within the block cave, based at least partly on the signaling received.

The signal processor or processing module may be configured to determine the location of rocks along with a degree of fragmentation of the rocks, based at least partly on the signaling received.

The apparatus may also include the array of acoustic sensors, including where the acoustic sensors include, or take the form of, electronic seismic sensors or optical fiber based sensors. The optical fiber based sensors may be configured so as to be multiplexed along a single fiber, enabling deployment and monitoring of a multiplicity of sensing devices.

The signal processor or processing module may be configured to map out the progression of ore material passing down through the block cave to the bottom of the block cave, including mapping out voids or stuck areas of a block of ore in the block cave.

According to some embodiments of the present invention, the signal processor or processing module may be configured with at least one processor and at least one memory including computer program code, the at least one memory and computer program code configured, with the at least one processor, to cause the apparatus at least to receive the signaling and determine the information about the ore being mined from the block cave in the block caving process.

The Method

According to some embodiments, the present invention may include, or take the form of, a method or process that includes steps for receiving with a signal processing module signaling containing information about detected acoustic emissions related to ore being mined from a block cave in a block caving process, including falling ore that creates unique acoustic signatures; and determining with the signal processing module information about the ore being mined from the block cave in the block caving process, based at least partly on the signaling received.

The method may also includes one or more of the features set forth herein, according to some embodiments of the present invention.

BRIEF DESCRIPTION OF THE DRAWING

The drawing includes FIGS. 1-3, which are not necessarily drawn to scale, as follows:

FIG. 1 is a block diagram of apparatus, according to some embodiments of the present invention.

DETAILED DESCRIPTION OF BEST MODE OF THE INVENTION

FIG. 1: The Basic Apparatus 10

FIG. 1 shows apparatus 10 having a signal processor 10a configured at least to receive signaling containing information about detected acoustic emissions related to ore being mined from a block cave in a block caving process, including falling ore that creates unique acoustic signatures; and determine information about the ore being mined from the block cave in the block caving process, based at least partly on the signaling received.

The signal processor 10a may also be configured to provide corresponding signaling containing corresponding information about the ore being mined from the block cave in the block caving process, including where the corresponding information includes information about a distribution and/or size of the ore being mined from the block cave in the block caving process. The scope of the invention is not intended to be limited to the type or kind of use of the corresponding signaling containing information about the ore being mined from the block cave in the block caving process, including for further processing, printing or displaying, as well as for other types or kinds of uses either now known or later developed in the future. Embodiments are also envisioned in which the corresponding signaling contains information that may be used for controlling the block caving process.

The apparatus 10 may also include other circuits, components or modules 10b to implement the functionality of the signal processor 10a either now known or later developed in the future, e.g., including memory modules, input/output modules, data and busing architecture and other signal processing circuits, wiring or components, consistent with that set forth herein.

FIG. 2

By way of example, according to the present invention, one method of determining these parameters or information related to the ore being mined from the block cave in the block caving process would be through the use of seismic acoustic sensing. Both a passive and an active sensing approach may be used to accurately monitor the block caving process, consistent with that set forth herein. In a typical configuration, an array of acoustic sensors may be placed surrounding the block cave.

Figure 2:
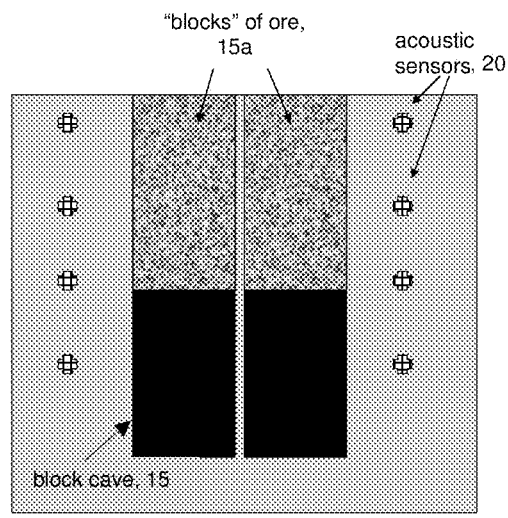
FIG. 2 is a diagram of a configuration having acoustic sensors arranged in relation to a block cave having one or more blocks of ore, according to some embodiments of the present invention.
Figure 3:
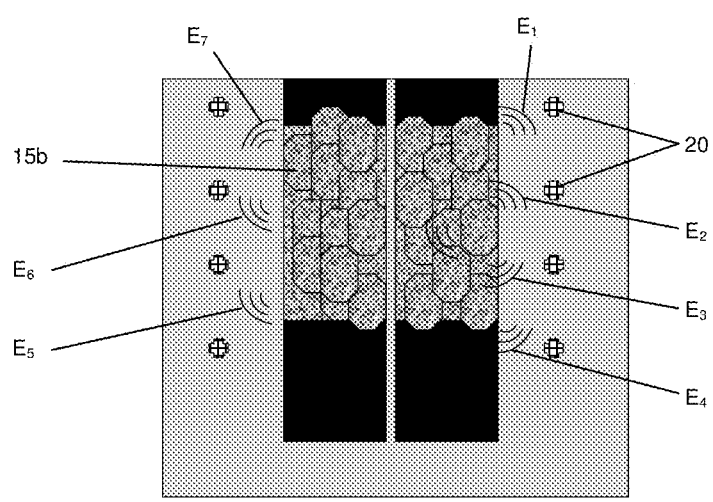
FIG. 3 is a diagram showing how, once a block caving process has begun, acoustic emissions of falling ore will create acoustics that can be detected by surrounding acoustic sensors, according to some embodiments of the present invention.

In particular, FIG. 2 shows a simplified diagram of a typical configuration for implementing the present invention in a block cave 15 having blocks of ore 15a. By way of example, in FIG. 2 an array of acoustic sensors 20 surround the block caving area in both the vertical and horizontal directions. These arrays of acoustic sensors 20 can be used with array processing algorithms to locate the origins of acoustic energy. FIG. 3 shows how, once the block caving process has begun, acoustic emissions indicated by reference labels e1, e2, e3, e4, e5, e6, e7 of the falling ore 15b will create acoustics that can be detected by all the surrounding acoustic sensors 20.

The falling ore 15b will create unique acoustic signatures. These acoustic signals will be detected by the acoustic sensors 20 at slightly different times depending on the distance of the individual acoustic generators (i.e. the falling and crushing rock) from the acoustic sensors 20. Array processing algorithms can then be used by the signal processor or processing module 10a to localize the signatures providing information on the locations of the emissions. From the acoustic data, a 3-dimensional map can be constructed by the signal processor or processing module 10a which details the origins of the acoustic sources and therefore the progression of the ore as it moves down the block cave 15. Stuck rock formations will not behave as an acoustic source, permitting the detection of regions by the signal processor or processing module 10a where the process is not progressing uniformly.

An important aspect of the block caving process is that as the ore falls it begins to crush the rock, which is required for the final separation of the target material from the gangue. For optimum extraction, a target particle size is desired and requires the rock to be crushed to small particles, often in the region of about 150 microns is diameter. Using the same acoustic data described above, the degree of crushing can also be determined by the signal processor or processing module 10a as the ore moves. In this case, the frequency components of the acoustically generated signals can be correlated by the signal processor or processing module 10a to the size of the rocks as they fall and strike each other. Smaller size rocks will typically create higher frequency components in their acoustic signatures allowing detection of these components through Fourier analysis of the received signals.

With these two components a full 3-d picture of the ore can be determined by the signal processor or processing module 10a with information on the rock progression as it falls, along with rock size in each area of the block.

In addition to the above mentioned passive acoustic sensing approach, a more traditional active seismic acoustic technique can be used. In this approach, an active acoustic source may be used to produce acoustic energy, these acoustic waves impinge on the block of ore and reflect back when the acoustics can then be sensed by the arrays of acoustic sensors 20. From the reflected acoustic energy, the location of the rocks can be determined by the signal processor or processing module 10a along with the degree of fragmentation of the rock. This system could resemble an acoustic tomography system where pairs of acoustic transmitters/receivers can alternately source and receive the acoustic signals. The received signals can be processed through algorithms by the signal processor or processing module 10a to determine the distribution and size of the rocks within the cave.

A wide variety of acoustic sensors can be used to monitor the acoustic signals. For example, these can range from the traditional electronic seismic sensors to very sensitive optical fiber based sensors. One particular advantage of the optical fiber sensors is the ability to multiplex many sensors along a single fiber, enabling the deployment and monitoring of a large number of devices.

Signal Processor or Signal Processing Module 10a

By way of example, and consistent with that described herein, the functionality of the signal processor, device or module 10a may be implemented to receive the signaling, process the signaling, and/or provide the corresponding signaling, using hardware, software, firmware, or a combination thereof, although the scope of the invention is not intended to be limited to any particular embodiment thereof. In a typical software implementation, the signal processor, device or module 10a may include, or take the form of, one or more microprocessor-based architectures having a microprocessor, a random access memory (RAM), a read only memory (ROM), input/output devices and control, data and address busing architecture connecting the same. A person skilled in the art would be able to program such a microprocessor-based implementation to perform the functionality set forth herein, as well as other functionality described herein without undue experimentation. The scope of the invention is not intended to be limited to any particular implementation using technology either now known or later developed in the future. Moreover, the scope of the invention is intended to include a signal processor, device or module 10a as either part of the aforementioned apparatus, as a stand alone module, or in the combination with other circuitry for implementing another module.

Techniques for receiving signaling in such a signal processor, device or module 10a are known in the art, and the scope of the invention is not intended to be limited to any particular type or kind thereof either now known or later developed in the future. Based on this understanding, a person skilled in the art would appreciate, understand and be able to implement and/or adapt the signal processor, device or module 10a without undue experimentation so as to receive signaling containing information about detected acoustic emissions related to ore being mined from a block cave in a block caving process, including falling ore that creates unique acoustic signatures, consistent with that set forth herein.

Techniques, including techniques based on array signal processing, for determining information based on analyzing or processing signaling received in such a signal processor, device or module 1oa are also known in the art, and the scope of the invention is not intended to be limited to any particular type or kind thereof either now known or later developed in the future. Based on this understanding, a person skilled in the art would appreciate, understand and be able to implement and/or adapt the signal processor, device or module 10a without undue experimentation so as to determine information about the ore being mined from the block cave in the block caving process, based at least partly on the signaling received, consistent with that set forth herein.

It is also understood that the apparatus 10 may include one or more other modules, components, processing circuits, or circuitry 10b for implementing other functionality associated with the underlying apparatus that does not form part of the underlying invention, and thus is not described in detail herein. By way of example, the one or more other modules, components, processing circuits, or circuitry may include random access memory, read only memory, input/output circuitry and data and address buses for use in relation to implementing the signal processing functionality of the signal processor, or devices or components, etc.

Array Processing Algorithms or Processing of Signaling

Array processing algorithms and techniques are known in the art for processing signaling containing information about acoustic emissions and determining information about the source of the acoustic emissions, based at least partly on the signaling received. By way of example, the acoustic emissions may be generated by an acoustic source (e.g., the falling ore) and information may be determined about the acoustic source, based at least partly on the signaling received. Alternatively, the acoustic emissions may be either generated by an acoustic source and reflected off another element, e.g., the ore, and information may be determined about the other element, e.g., the ore, based at least partly on the signaling received.

By way of example, array processing algorithms and techniques known in the art may include that disclosed in U.S. Pat. Nos. 8,336,393 and 7,882,750, which are assigned to the assignee of the instant patent application, and hereby incorporated by reference in their entirety. Other array processing algorithms and techniques known in the art may include that disclosed in U.S. Pat. No. 7,471,592, as well as which is also hereby incorporated by reference in their entirety. See also array processing algorithms and techniques known in the art and disclosed in a technical article by A. Nehorai et al., entitled, "Acoustic Vector-sensor array processing," IEEE Transactions on Signal Processing, Vol. 42, No. 9, September 1994, which is also incorporated by reference in its entirety. Moreover, the scope of the invention is intended to include using other types or kinds of array processing algorithm and technique either now known or later developed in the future. Finally, the scope of the invention is not intended to be limited to any particular type or kind of array processing algorithm and technique either now known or later developed in the future.

A person skilled in the art without undue experimentation would be able to adapt one or more of the aforementioned array processing algorithms and techniques in order to implement the present invention, including to configure a signal processing module at least to receive signaling containing information about detected acoustic emissions related to ore being mined from a block cave in a block caving process, including falling ore that creates unique acoustic signatures; and determine information about the ore being mined from the block cave in the block caving process, based at least partly on the signaling received.

Finally, Fourier processing algorithms and techniques are also known in the art for processing signaling in order to implement the present invention, and the scope of the invention is not intended to be limited to any particular type or kind thereof either now known or later developed in the future.

Applications

The present invention may also be used in, or form part of, or used in conjunction with, industrial processes like a mineral extraction processing system for extracting minerals from ore using block caving that are either now known or later developed in the future, including any mineral process, such as those related to processing substances or compounds that result from inorganic processes of nature and/or that are mined from the ground, as well as including either other extraction processing systems or other industrial processes, where the extraction, or sorting, or classification, of product by size is critical to overall industrial process performance.

THE SCOPE OF THE INVENTION

While the invention has been described with reference to an exemplary embodiment, it will be understood by those skilled in the art that various changes may be made and equivalents may be substituted for elements thereof without departing from the scope of the invention. In addition, may modifications may be made to adapt a particular situation or material to the teachings of the invention without departing from the essential scope thereof. Therefore, it is intended that the invention not be limited to the particular embodiment(s) disclosed herein as the best mode contemplated for carrying out this invention.

What is claimed is:

1. A mineral extraction processing system for monitoring a block caving process, comprising:
   acoustic sensors arranged to monitor a block cave in a block caving process, sense acoustic emissions of falling ore being mined from the block cave that create unique acoustic signatures, and provide signaling containing information about the acoustic emissions sensed; and
   a signal processing module configured at least to:
   receive the signaling; and
   determine corresponding signaling containing information about a 3-dimensional map that details origins of acoustic sources of the acoustic emissions, and rock progression and size of the falling ore moving down from the block cave in the block caving process, based at least partly on the signaling received.

2. A mineral extraction processing system according to claim 1, wherein the signal processing module is configured to receive the signaling from an array of acoustic sensors placed around the block cave, including where the array of acoustic sensors surrounds the block cave in both vertical and horizontal directions.

3. A mineral extraction processing system according to claim 2, wherein the apparatus comprises the array of acoustic sensors.

4. A mineral extraction processing system according to claim 3, wherein the acoustic sensors comprise electronic seismic sensors or optical fiber based sensors.

5. A mineral extraction processing system according to claim 4, wherein the optical fiber based sensors are configured so as to be multiplexed along a single fiber, enabling deployment and monitoring of a multiplicity of sensing devices.

6. A mineral extraction processing system according to claim 1, wherein the signal processing module is configured to receive the signaling from an array of sensors detected at different times depending on the distance of individual acoustic generators from the array of sensors, including where the individual acoustic generators are falling and crushing rock.

7. A mineral extraction processing system according to claim 1, wherein the signal processing module is configured to use one or more array processing algorithms to localize the unique acoustic signatures providing information about locations of the detected acoustic emissions, based at least partly on the signaling received.

8. A mineral extraction processing system according to claim 1, wherein the signal processing module is configured to determine information about stuck rock formations that do not behave as an acoustic source, permitting detection of regions where the block caving process is not progressing uniformly, based at least partly on the signaling received.

9. A mineral extraction processing system according to claim 1, wherein the signal processing module is configured to determine a degree of crushing as the ore moves in the block cave, based at least partly on the signaling received.

10. A mineral extraction processing system according to claim 1, wherein the signal processing module is configured to correlate frequency components of acoustically generated signals to the size of rocks falling and striking each other, including where smaller sized rocks create higher frequency components in acoustic signatures and larger sized rocks create lower frequency components in the acoustic signatures, allowing detection of the frequency components through Fourier analysis of the signaling received.

11. A mineral extraction processing system according to claim 10, wherein the signal processing module is configured to determine a substantially full 3-dimensional image or picture of the ore that contains information on the progression of falling rock, along with rock size in each area of the block cave, based at least partly on the signaling received.

12. A mineral extraction processing system according to claim 1, wherein the signaling contains information about acoustic waves produced by an active acoustic source that impinge on a block of ore and reflect back acoustic energy sensed by an array of acoustic sensors.

13. A mineral extraction processing system according to claim 12, wherein the signal processing module is configured to determine the location of rocks along with a degree of fragmentation of the rocks, based at least partly on the signaling received.

14. A mineral extraction processing system according to claim 12, wherein the apparatus forms part of an acoustic tomography system configured with pairs of acoustic transmitters/receivers that can alternately source and receive acoustic signals.

15. A mineral extraction processing system according to claim 12, wherein the signal processing module is configured to process received acoustic signals and determine the distribution and size of the rocks within the block cave.

16. A mineral extraction processing system according to claim 1, wherein the signal processing module is configured to determine a distribution and size of rocks within the block cave, based at least partly on the signaling received.

17. A mineral extraction processing system according to claim 1, wherein the signal processing module is configured to determine the location of rocks along with a degree of fragmentation of the rocks, based at least partly on the signaling received.

18. A mineral extraction processing system according to claim 1, wherein the signal processing module is configured to map out the progression of ore material passing down through the block cave to the bottom of the block cave, including mapping out voids or stuck areas of a block of ore in the block cave.

19. A mineral extraction processing system according to claim 1, wherein the signal processing module is configured with at least one processor and at least one memory including computer program code, the at least one memory and computer program code configured, with the at least one processor, to cause the apparatus at least to receive the signaling and determine the information about the ore being mined from the block cave in the block caving process.

20. A mineral extraction processing system according to claim 1, wherein the signal processing module is configured to provide the corresponding signaling; including where the corresponding signaling includes information about a distribution and size of the ore being mined from the block cave in the block caving process.

21. A mineral extraction processing system according to claim 1, wherein the signal processing module is configured to provide the corresponding signaling as control signaling for controlling the block caving process.

22. A method for monitoring a block caving process in a mineral extraction processing system comprising:
arranging acoustic sensors to monitor a block cave in a block caving process, sense acoustic emissions of falling ore being mined from the block cave that create unique acoustic signatures, and provide signaling containing information about the acoustic emissions sensed; and
receiving, with a signal processing module, the signaling; and
determining, with the signal processing module, corresponding signaling containing information about a 3-dimensional map which details origins of acoustic sources of the acoustic emissions, and rock progression and size of the falling ore moving down from the block cave in the block caving process, based at least partly on the signaling received.

23. A method according to claim 22, wherein the method comprises receiving with the signal processor module the signaling from an array of acoustic sensors placed around the block cave, including where the array of acoustic sensors surrounds the block cave in both vertical and horizontal directions.

24. A method according to claim 23, wherein the method comprises coupling the array of acoustic sensors and the signal processor module.

25. A method according to claim 24, wherein the method comprises configuring the acoustic sensors as either electronic seismic sensors or optical fiber based sensors.

26. A method according to claim 25, wherein the method comprises multiplexing the optical fiber based sensors along a single fiber, enabling deployment and monitoring of a multiplicity of sensing devices.

27. A method according to claim 22, wherein the method comprises receiving with the signal processor module the signaling from an array of sensors detected at different times depending on the distance of individual acoustic generators from the array of sensors, including where the individual acoustic generators are falling and crushing rock.

28. A method according to claim 22, wherein the method comprises using in the signal processor module one or more array processing algorithms to localize the unique acoustic signatures providing information about locations of the detected acoustic emissions, based at least partly on the signaling received.

29. A method according to claim 22, wherein the method comprises determining with the signal processing module information about stuck rock formations that do not behave as an acoustic source, permitting detection of regions where the block caving process is not progressing uniformly, based at least partly on the signaling received.

30. A method according to claim 22, wherein the method comprises determining with the signal processing module a degree of crushing as the ore moves in the block cave, based at least partly on the signaling received.

31. A method according to claim 22, wherein the method comprises correlating with the signal processing module frequency components of acoustically generated signals to the size of rocks falling and striking each other, including where smaller sized rocks create higher frequency components in acoustic signatures and larger sized rocks create lower frequency components in the acoustic signatures, allowing detection of the frequency components through Fourier analysis of the signaling received.

32. A method according to claim 31, wherein the method comprises determining with the signal processing module a substantially full 3-dimensional image or picture of the ore that contains information on the progression of falling rock, along with rock size in each area of the block cave, based at least partly on the signaling received.

33. A method according to claim 22, wherein the method comprises receiving with the signal processor module the signaling containing information about acoustic waves produced by an active acoustic source that impinge on a block of ore and reflect back acoustic energy sensed by an array of acoustic sensors.

34. A method according to claim 33, wherein the method comprises determining with the signal processing module the location of rocks along with a degree of fragmentation of the rocks, based at least partly on the signaling received.

35. A method according to claim 33, wherein the method comprises using pairs of acoustic transmitters/receivers that can alternately source and receive acoustic signals and form part of an acoustic tomography system.

36. A method according to claim 33, wherein the method comprises processing with the signal processing module received acoustic signals and determining the distribution and size of the rocks within the block cave.

37. A method according to claim 22, wherein the method comprises determining with the signal processing module a distribution and size of rocks within the block cave, based at least partly on the signaling received.

38. A method according to claim 22, wherein the method comprises determining with the signal processing module the location of rocks along with a degree of fragmentation of the rocks, based at least partly on the signaling received.

39. A method according to claim 22, wherein the method comprises mapping out the progression of ore material passing down through the block cave to the bottom of the block cave, including mapping out voids or stuck areas of a block of ore in the block cave.

40. A method according to claim 22, wherein the method comprises configuring the signal processing module with at least one processor and at least one memory including computer program code, the at least one memory and computer program code configured, with the at least one processor, to cause the apparatus at least to receive the signaling and determine the information about the ore being mined from the block cave in the block caving process.

41. A method according to claim 22, wherein the method comprises providing the corresponding signaling, including where the corresponding signaling includes information about a distribution and size of the ore being mined from the block cave in the block caving process.

42. A method according to claim 22, wherein the method comprises providing from the signal processing module the corresponding signaling as control signaling for controlling the block caving process.

43. Apparatus for monitoring a block caving process comprising: means for acoustically monitoring a block cave in a block caving process, sensing acoustic emissions of falling ore being mined from the block cave that create unique acoustic signatures, and providing signaling containing information about the acoustic emissions sensed;

means for receiving the signaling; and means for determining corresponding signaling containing information about a 3-dimensional map which details origins of acoustic sources of the acoustic emissions, and rock progression and size of the falling ore moving down from the block cave in the block caving process, based at least partly on the signaling received.

44. Apparatus according to claim 43, wherein the apparatus comprises means for providing the corresponding signaling, including where the corresponding signaling includes information about a distribution and size of the ore being mined from the block cave in the block caving process.

* * * * *